(12) United States Patent
Bauer et al.

(10) Patent No.: US 10,298,471 B2
(45) Date of Patent: May 21, 2019

(54) SYSTEMS AND METHODS FOR PROVIDING DEVICE USAGE DATA

(71) Applicant: The Gillette Company, Boston, MA (US)

(72) Inventors: Matthew Stephen Bauer, Loveland, OH (US); Pawan Sudarshan Kodandapani, Boston, MA (US); Jeffrey Dean McDowell, Hingham, MA (US); Eric Viveros Borges, Plymouth, MA (US); Gordon Allen Briggs, Johnston, RI (US)

(73) Assignee: The Gillette Company LLC, Boston, MA (US)

( * ) Notice: Subject to any disclaimer, the term of this patent is extended or adjusted under 35 U.S.C. 154(b) by 131 days.

(21) Appl. No.: 15/215,641

(22) Filed: Jul. 21, 2016

(65) Prior Publication Data

US 2017/0099199 A1 Apr. 6, 2017

Related U.S. Application Data

(60) Provisional application No. 62/237,136, filed on Oct. 5, 2015.

(51) Int. Cl.
*H04L 12/28* (2006.01)
*H04L 12/26* (2006.01)
(Continued)

(52) U.S. Cl.
CPC .......... *H04L 43/065* (2013.01); *A61C 17/221* (2013.01); *B26B 21/4056* (2013.01);
(Continued)

(58) Field of Classification Search
CPC .......................... H04L 12/2823; H04L 43/065
See application file for complete search history.

(56) References Cited

U.S. PATENT DOCUMENTS 8,061,041 B2 11/2011 Jessemey et al.
8,122,606 B2 2/2012 Hart
(Continued)

FOREIGN PATENT DOCUMENTS

WO WO 2009/076301 6/2009
WO WO 2009/076415 6/2009

OTHER PUBLICATIONS

PCT International Search Report with Written Opinion in corresponding international application PCT/US2016/055254 dated Dec. 23, 2016.
(Continued)

*Primary Examiner* — Jerry B Dennison
(74) *Attorney, Agent, or Firm* — John M. Lipchitz

(57) ABSTRACT

Included are embodiments of a system for monitoring device usage. The system may include a handheld device for performing an action, where the handheld device includes an engagement sensor and a computer that includes a processor and a memory component. The memory component stores logic that causes the computer to determine a minimum device engagement time of the handheld device. In some embodiments, the logic causes the computer to receive output data from the engagement sensor, where the output data includes an actual device engagement time, determine if the actual device engagement time is at least as long as the minimum device engagement time, and in response to determining that the actual device engagement time is at least as long as the minimum device engagement time, determine the action taken by the handheld device.

20 Claims, 7 Drawing Sheets

(51) Int. Cl.
*H04L 29/08* (2006.01)
*A61C 17/22* (2006.01)
*B26B 21/40* (2006.01)
*H04W 4/80* (2018.01)
*A46B 15/00* (2006.01)
*G07C 3/04* (2006.01)

(52) U.S. Cl.
CPC .......... *H04L 12/2823* (2013.01); *H04L 67/22* (2013.01); *A46B 15/001* (2013.01); *A46B 15/0006* (2013.01); *A46B 15/0008* (2013.01); *G07C 3/04* (2013.01); *H04W 4/80* (2018.02)

(56) References Cited

U.S. PATENT DOCUMENTS

| | | | |
|---|---|---|---|
| 8,230,600 B2 | 7/2012 | Hart et al. | |
| 8,510,958 B2 | 8/2013 | Hart et al. | |
| 8,585,411 B2* | 11/2013 | Puurunen | A46B 15/0006 15/167.1 |
| 9,027,192 B1* | 5/2015 | Cole | A46B 15/0004 15/105 |
| 9,072,370 B2* | 7/2015 | Gatzemeyer | A46B 15/0002 |
| 9,757,065 B1* | 9/2017 | Suri | A61B 5/4833 |
| 2007/0050983 A1 | 3/2007 | Schnak et al. | |
| 2008/0052911 A1 | 3/2008 | Kohler | |
| 2008/0052912 A1* | 3/2008 | Barry | A45D 27/29 30/41.7 |
| 2008/0146887 A1* | 6/2008 | Rao | A46B 7/04 600/300 |
| 2008/0189953 A1 | 8/2008 | Jessemey et al. | |
| 2008/0289185 A1 | 11/2008 | Clarke | |
| 2009/0071008 A1 | 3/2009 | Hart et al. | |
| 2009/0071010 A1 | 3/2009 | Hart | |
| 2009/0119923 A1 | 5/2009 | Hart et al. | |
| 2009/0215015 A1* | 8/2009 | Chu | G09B 19/0084 434/238 |
| 2009/0241278 A1* | 10/2009 | Lemchen | A46B 15/0002 15/105 |
| 2009/0320227 A1 | 12/2009 | Cohen et al. | |
| 2010/0015589 A1* | 1/2010 | Lehavi | G09B 23/283 434/263 |
| 2010/0031510 A1 | 2/2010 | Gester et al. | |
| 2012/0266465 A1 | 10/2012 | Hart et al. | |
| 2013/0000670 A1* | 1/2013 | Binner | A46B 15/0006 134/6 |
| 2015/0068043 A1 | 3/2015 | Gester et al. | |
| 2015/0230899 A1 | 8/2015 | Vetter et al. | |
| 2016/0143718 A1* | 5/2016 | Serval | A46B 15/0022 15/22.1 |
| 2016/0235357 A1* | 8/2016 | Ohmer | A46B 15/0006 |
| 2017/0097758 A1* | 4/2017 | Bauer | B26B 21/4056 |
| 2017/0099199 A1* | 4/2017 | Bauer | H04L 43/065 |

OTHER PUBLICATIONS

U.S. Appl. No. 15/215,650, filed Jul. 21, 2016, Matthew Stephen Bauer et al.

* cited by examiner

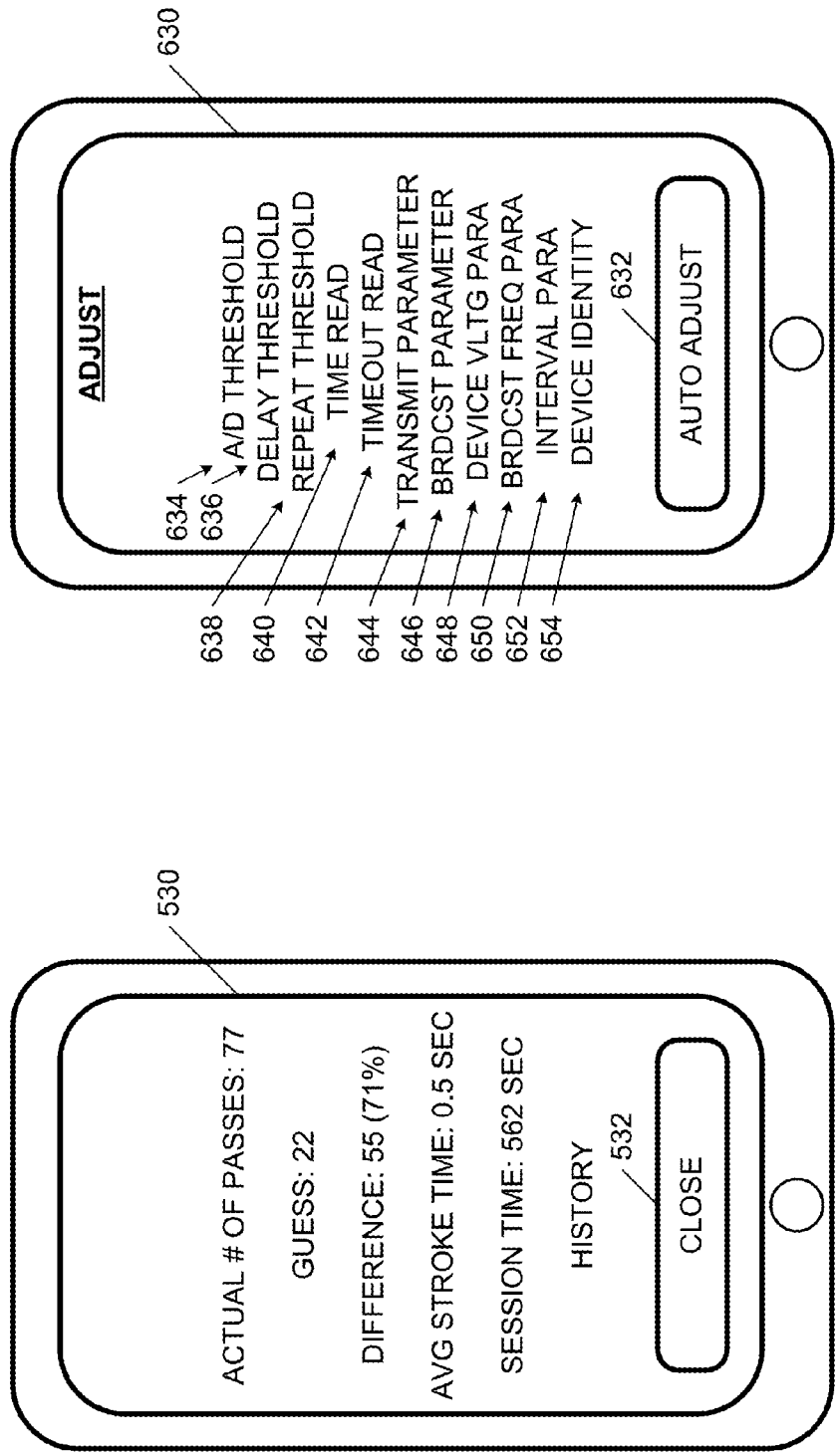

SYSTEMS AND METHODS FOR PROVIDING DEVICE USAGE DATA

FIELD OF THE INVENTION

The present application relates generally to systems and methods for monitoring device usage and providing device tuning; and specifically to systems and methods that facilitate communication among a handheld device, a user device, and a remote computing device for monitoring usage data and providing tuning options related to the handheld device.

BACKGROUND OF THE INVENTION

While many people utilize handheld devices, such as toothbrushes and razors, oftentimes the user does not recognize when to change a replacement part, such as a toothbrush head or a razor cartridge. As such, the handheld device may often not operate optimally. Additionally, the user may be improperly utilizing the handheld device to maximize life of the handheld device and/or provide optimal results when in use. Accordingly, a need exists in the industry.

SUMMARY OF THE INVENTION

Included are embodiments of a system for monitoring device usage. The system may include a handheld device for performing an action, where the handheld device includes an engagement sensor and a computer that includes a processor and a memory component. The memory component may store logic that, when executed by the processor causes the computer to determine a minimum device engagement time of the handheld device, where the minimum device engagement time relates to a duration for a single pass of the handheld device in an active state. In some embodiments, the logic causes the computer to receive output data from the engagement sensor, where the output data includes an actual device engagement time, determine if the actual device engagement time is at least as long as the minimum device engagement time, and in response to determining that the actual device engagement time is at least as long as the minimum device engagement time, determine the action taken by the handheld device. In some embodiments, the logic causes the computer to provide data related to the action taken by the handheld device for display.

Also included are embodiments of a method. Some embodiments of the method include determining a minimum razor engagement time of a razor device, where the minimum razor engagement time relates to a minimum duration required for counting a single stroke of the razor device across an length of skin, receiving stroke data related to an actual stroke of the razor device across the length of skin, where the stroke data includes an actual duration of the actual stroke of the razor device across the length of skin, and determining if the actual duration is at least as long as the minimum duration. Some embodiments may be configured to, in response to determining that the actual duration is at least as long as the minimum duration, determine an action taken by the razor device from the stroke data. Some embodiments may be configured to provide data related to the action taken by the razor device for display.

Also included are embodiments of a non-transitory computer-readable medium. Some embodiments of the non-transitory computer-readable medium include logic that, when executed by a computer, causes the computer to determine a minimum device engagement time of a handheld device, where the minimum device engagement time relates to a duration for a single pass of the handheld device in an active state, and where the handheld device includes an engagement sensor for determining when the handheld device is engaged. In some embodiments, the logic causes the computer to receive output data from the engagement sensor, where the output data relates to actual device engagement time, determine if the actual device engagement time is at least as long as the minimum device engagement time, and in response to determining that the actual device engagement time is at least as long as the minimum device engagement time, determine an action taken by the handheld device. In some embodiments, the logic causes the computer to provide data related to the action for display.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

FIG. 5 depicts a user interface for providing data regarding usage of a handheld device, according to embodiments described herein;

FIG. 6 depicts a user interface for providing options for device tuning, according to embodiments described herein;

DETAILED DESCRIPTION OF THE INVENTION

Embodiments disclosed herein include systems and methods for device monitoring and device tuning. As an example, some embodiments may be configured to receive a signal from an engagement sensor on a handheld device and determine whether the signal indicates that the handheld device has been used. As an example, if the handheld device is a straight razor, the signal may be related to pressure of the razor against a user's skin. Similarly, the signal may be in response to the razor being positioned or moved in a certain manner indicative of being in use, regardless, if the time that the handheld device is engage may be timed and compared with a minimum engagement time to determine whether the signal indicates an actual stroke or whether the signal is likely a false signal. This data may be accumulated until it is determined that the shaving session is complete. Determining that the shaving session is complete may include a timeout after nonuse, a timeout from start of the session until a predicted end time, a predetermined number of strokes and a timeout, an actuation of a power switch, and/or others.

Regardless, the handheld device may include hardware and/or software to communicate with another computer, such as a mobile device. The mobile device may receive the data and provide one or more user interfaces related to the number of strokes taken, the time per stroke, the session time, and/or other data. Some embodiments provide an option for the user to guess the number of strokes taken, which is then compared with the actual number of strokes taken. This may assist the user in more accurately determining when to replace a razor cartridge, a razor, and/or other assisting device. The data may also be used to provide instructions to the user to more effectively use the handheld device. As an example, if the stroke speed is too fast, the angle of the stroke is incorrect, the temperature of the water used is too hot, the user uses too many or too few strokes, etc. the handheld device and/or mobile device may indicate the issue and/or solution to the user.

Embodiments described herein may also be configured to determine settings for the handheld device for tuning the handheld device. As an example, a minimum stroke time for counting a stroke may be provided to a user via the mobile device. In some embodiments, the mobile device may also provide options for the user to alter one or more of the settings. In some embodiments, there is an option for automatic calibration, based on data received from the handheld device. These and other embodiments are also described in more detail below.

Figure 1:
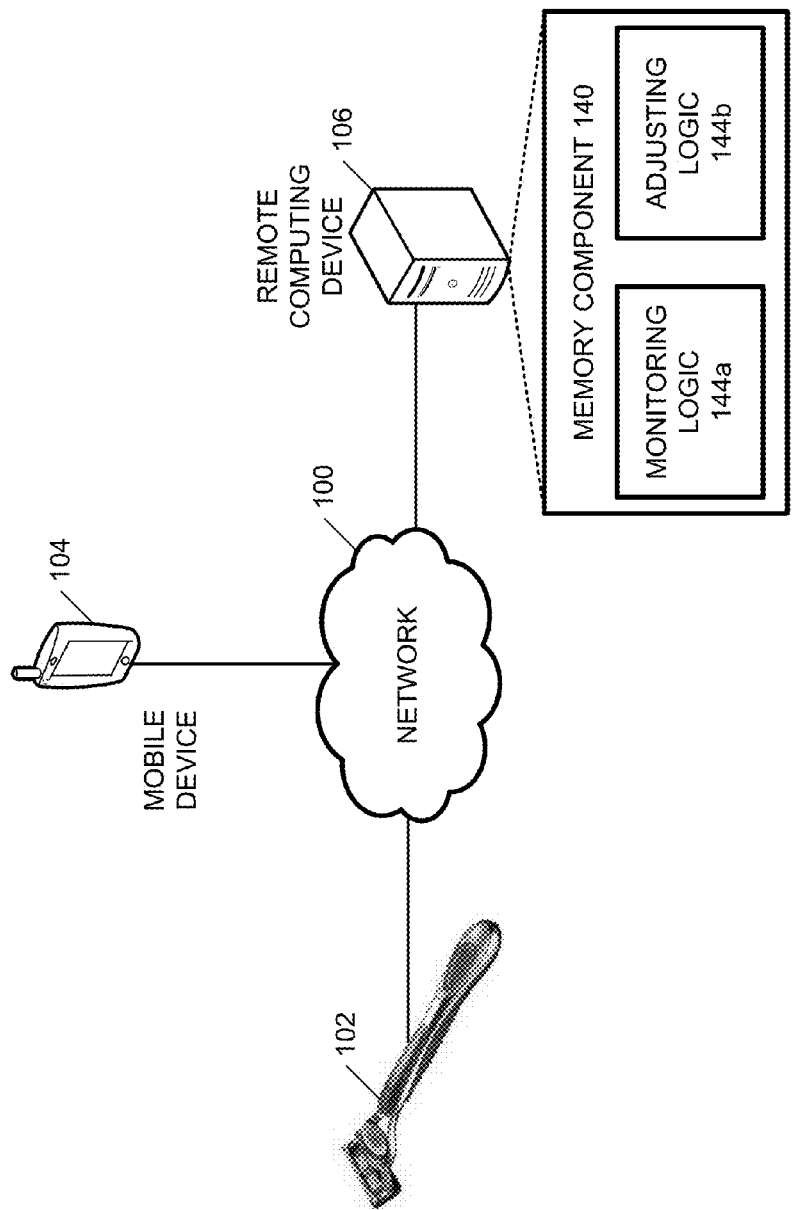
FIG. 1 depicts a communication environment for monitoring device usage and device tuning, according to embodiments described herein.

Referring now to the drawings, FIG. 1 depicts a communication environment for monitoring device usage and device tuning, according to embodiments described herein. As illustrated, the communication environment includes a network 100, which communicatively couples a handheld device 102, a mobile device 104, a remote computing device 106, and/or other device. As such, the network 100 may include a wide area network, such as the internet, a public switched telephone network, a cellular network, and the like. Similarly, the network 100 may include a local area network, such as an Ethernet or wireless fidelity. In some embodiments, the network 100 may include a direct device-to-device communications protocol, such as Bluetooth™, near field communication, and/or the like.

Also depicted in FIG. 1 is the handheld device 102. The handheld device 102 may include a face razor, a body razor, a toothbrush, a skin treatment device, and/or other devices. As such, the handheld device 102 may be a powered device (such as an electric razor or electric toothbrush) or an unpowered device (such as a straight razor or traditional toothbrush). Regardless, the handheld device 102 may be configured to communicate with the mobile device 104 and/or the remote computing device 106.

The mobile device 104 may include any computer or computing device, such as a smart phone, personal computer, laptop, tablet, wearable device, and the like. As discussed in more detail below, the mobile device 104 may include a memory component, a processor, and logic for providing user interfaces, options, and data related to the handheld device 102. While not specifically depicted, the mobile device 104 may include some or all of the hardware (and/or software) components depicted and described for the remote computing device 106 in FIGS. 1 and 9.

The remote computing device 106 may communicate with the handheld device 102 and/or the mobile device 104 and may be configured as a server, personal computer, or other computing device for providing the functionality described herein. Accordingly, the remote computing device 106 may include a memory component 140 for storing monitoring logic 144a and adjusting logic 144b. As described in more detail below, the monitoring logic 144a, when executed by a processor, causes a communication with the handheld device 102 to monitor usage and make other determinations described herein. The adjusting logic 144b may similarity facilitate adjustments to the handheld device 102 and/or the monitoring parameters of the handheld device 102. As such, while the monitoring logic 144a and the adjusting logic 144b are depicted as residing in the remote computing device 106, in some embodiments, the monitoring logic 144a, the adjusting logic 144b, and/or counterpart logic may reside on the handheld device 102 and/or the mobile device 104.

Figure 2:
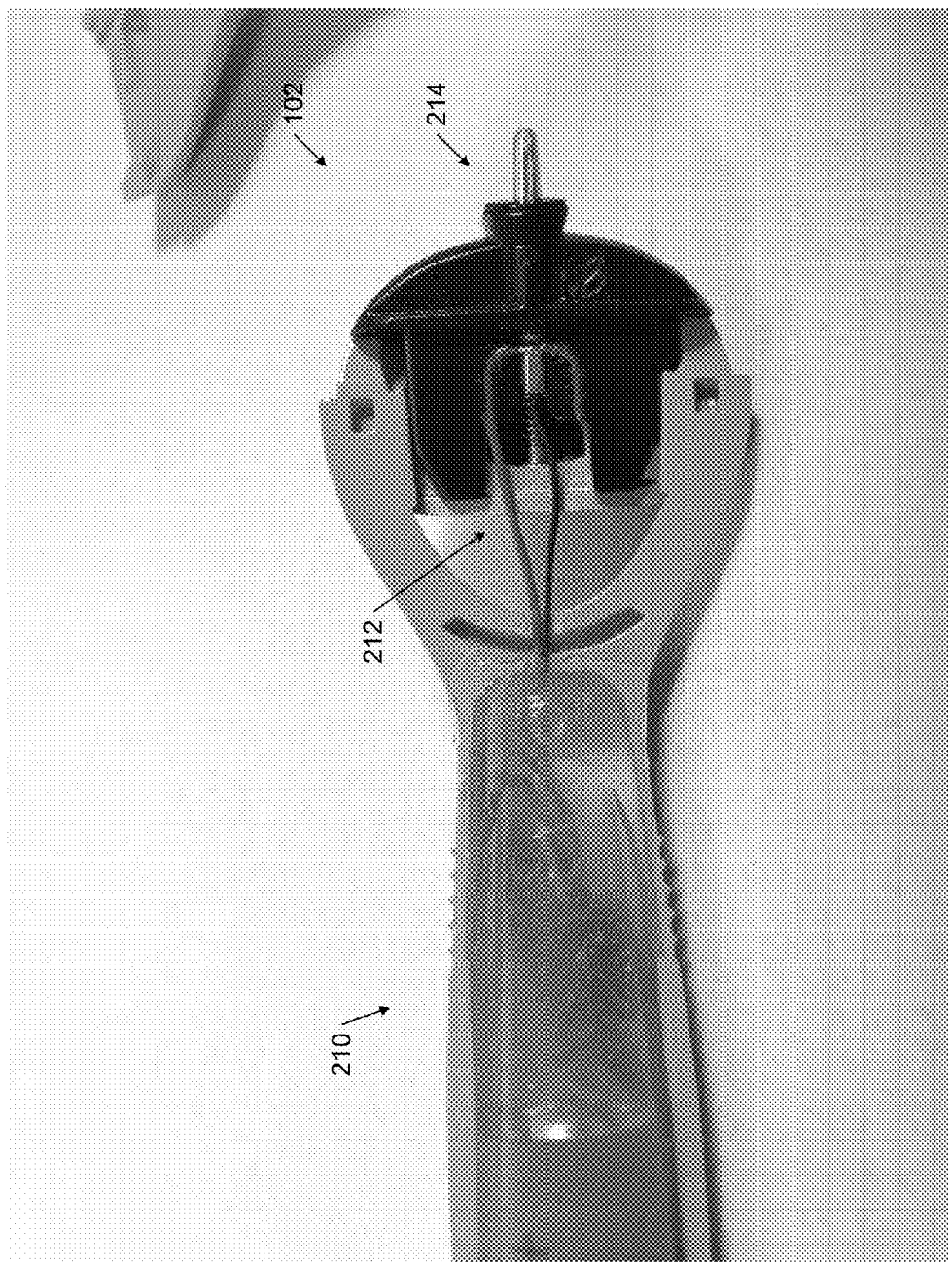
FIG. 2 depicts a handheld device for monitoring device usage and device tuning, according to embodiments described herein.

FIG. 2 depicts a handheld device 102 for monitoring device usage and device tuning, according to embodiments described herein. As illustrated, the handheld device 102 may include a handle portion 210, a sensing system 212, and a cartridge connection component 214. The handle portion 210 may include structure to facilitate a user holding the handheld device 102. The handle portion 210 may include also a transmitting system, which may include a transmitter, a receiver, and/or other hardware and software for communicating with the mobile device 104 and/or the remote computing device 106. The transmitting system may also be electrically coupled to a local computing device, which may be configured as an integrated computing device. The local computing device may include a memory component, a processor, and/or other computing components in the handle portion 210 that executes software for facilitating this communication. The handle portion 210 may include a reservoir for receiving water and/or any assisting substance type (such as shaving cream, toothpaste, etc.) and determining the resistivity of the received substances.

As an example, some embodiments may be configured to receive environment data related to a water type, an assisting substance type (which may include a shaving prep type), a distance from the handheld device, data related to interference with the handheld device and/or other environment data. Additionally, the handheld device 102 and/or mobile device 104 may automatically adjust the first operating parameter and/or the second operating parameter based on the environment data.

The sensing system 212 may include one or more engagement sensors such as a depression sensor, a gyroscope, an accelerometer, a temperature sensor and/or other sensors for determining whether the handheld device 102 is in use. The sensing system 212 may be electrically coupled to the local computing device in the handle portion 210 and may be configured to detect an engagement of the handheld device 102. As an example, FIG. 2 depicts a razor device with the sensing system 212 configured as a depression sensor, such that when the razor device is pressed against a user's skin, the depression sensor is triggered. Some embodiments of the sensing system 212 may include a timer for determining a length of time that the engagement sensor is activated. Accordingly, the sensing system 212 may detect a position, an angle, and/or a movement of the handheld device 102 and may communicate that information to the transmitting system (such as via the local computing device).

The cartridge connection component 214 may be configured to receive a cartridge (such as a brush head, a razor cartridge, etc., depending on the embodiment). Additionally, the cartridge connection component 214 may connect with the sensing system 212 for communicating usage data from the cartridge to the handle portion 210.

It should be understood that some embodiments may be further configured to communicate with an assisting device, such as a shave prep container, as tooth paste container, a replacement razor, a replacement toothbrush head, a razor device container, a toothbrush container, etc. for making other determinations and/or adjustments. As an example, the handheld device 102 and/or the mobile device 104 may communicate with computing components connected to the shave prep container to determine an amount of shave prep used by the user, a timing of use of the shave prep, and/or other information. Based on this information, the handheld device 102 and/or mobile device 104 may make adjustments to settings (such as the minimum duration for counting a stroke) and/or provide other data to the user.

Figure 3:
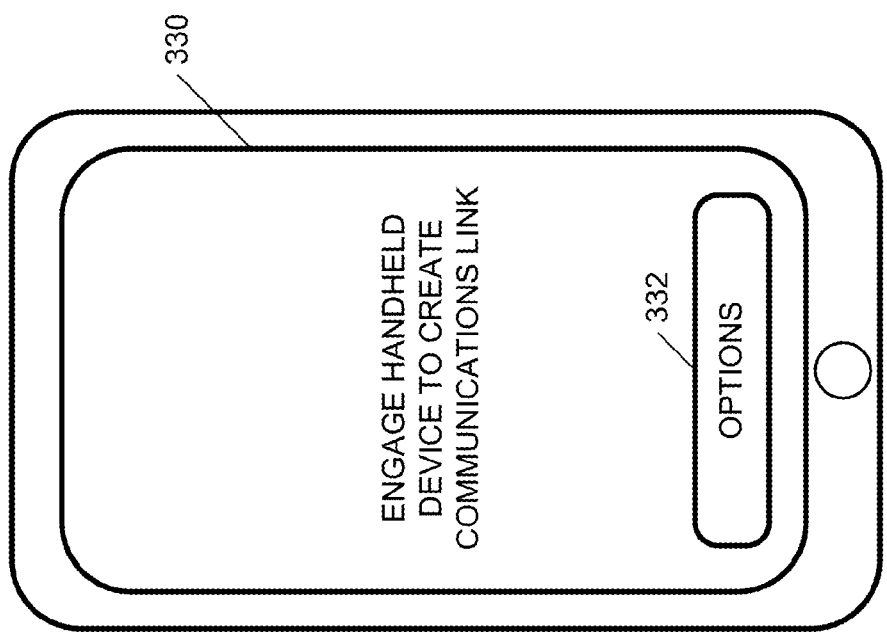
FIG. 3 depicts a user interface that may be provided for monitoring device usage, according to embodiments described herein.

FIG. 3 depicts a user interface 330 that may be provided for monitoring device usage, according to embodiments described herein. As illustrated, the user interface 330 may be configured to begin detection of use of the handheld device 102. Specifically, the mobile device 104 may be configured to provide one or more applications, such as a monitoring application and adjustments application (which may be provided via the monitoring logic 144a and the adjusting logic 144b, respectively). In response to selection of the monitoring application, the mobile device 104 may link with the handheld device 102 such that when the handheld device 102 is activated and/or engaged, the mobile device 104 may receive data from the handheld device 102. The data received may include data regarding the number of passes the handheld device 102 makes, a duration of strokes, and/or other data. Accordingly, the user interface 330 may provide instructions regarding initiating the linkage between the handheld device 102 and the mobile device 104. The user interface 330 may also include an options option 332, which may provide additional options related to device monitoring and/or device tuning.

Is should be understood that in some embodiments, the handheld device 102 may be configured to automatically begin monitoring usage with or without connection to the mobile device 104 or the remote computing device 106. Specifically, the handheld device 102 may be configured with memory to store usage data such that if/when the handheld device 102 connects with the mobile device 104 and/or remote computing device 106, the data may be communicated at that time.

Figure 4:
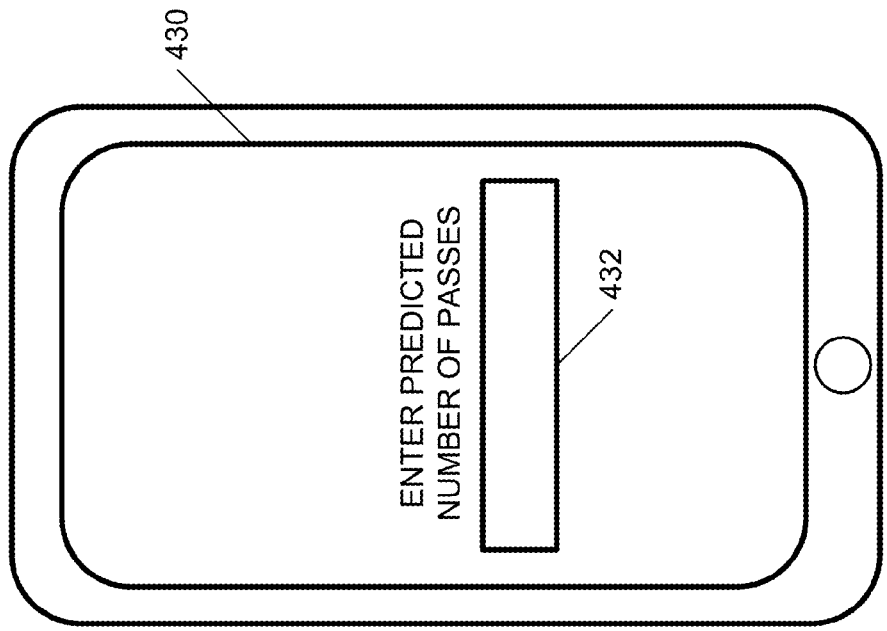
FIG. 4 depicts a user interface that may be provided for a user to predict a number of passes with a handheld device, according to embodiments described herein.

FIG. 4 depicts a user interface 430 that may be provided for a user to predict a number of passes with a handheld device 102, according to embodiments described herein. As illustrated, the user interface 430 may provide a prediction field 432 for a user to enter a predicted total number of passes that the user believes was made during a shaving session, a tooth brushing session, or other session. As an example, a user may activate the device and monitoring application. The user may then shave his face with the handheld device 102. After completion of the shave, the handheld device 102 and/or the mobile device 104 may determine a number of passes or strokes made during the shave. Additionally, the user interface 430 may provide the prediction field 432 for the user to enter the number of strokes that the user believes he took during the shave.

FIG. 5 depicts a user interface 530 for providing data regarding usage of a handheld device 102, according to embodiments described herein. As illustrated, the user interface 530 may provide monitoring data related to one or more previous activity (such as a shave, a tooth brushing session, etc.) of the handheld device 102. Specifically, upon completion of a session, data related to the session may be provided to the mobile device 104. This data may include a number of passes (or strokes, rotations, etc.) made during a session, the predicted number passes entered into the prediction field 432 (FIG. 4), a difference between the actual number of passes and the predicted number of passes, an average pass time, a session time, and historical data. The total number of engagements (such as strokes, passes, rotations, etc.) may also be communicated to the remote computing device 106.

As an example, the number of engagements may be sent from the handheld device 102 to the mobile device 104 (and/or the remote computing device 106). In some embodiments, the number of engagements may be determined based on a number of times that the engagement sensor is triggered. However, some embodiments may be configured to only count a number of times that the engagement sensor is triggered for a predetermined amount of time. This may prevent the counting of engagements, when the engagement sensor is inadvertently triggered.

Additionally, the handheld device 102 may communicate at least a portion of this data to the remote computing device 106. In some embodiments, the remote computing device 106 may receive the stroke data (and other data) from the handheld device 102. The remote computing device 106 may perform analysis on the data and communicate with the mobile device 104 to provide the data in the user interface 530 (and other user interfaces). Similarly, some embodiments, the handheld device 102 may communicate directly with the mobile device 104 to provide the data. In these embodiments, the remote computing device 106 may provide cloud-based services and storage for the data across multiple devices.

FIG. 6 depicts a user interface 630 for providing options for device tuning, according to embodiments described herein. As illustrated, the user interface 630 may provide an auto adjust option 632, as well as options 634-654 for adjusting settings on the handheld device 102. The options 634-654 may include an analog to digital (A/D) threshold option 634, a delay threshold option 636, a repeat threshold option 638, a time read option 640, a timeout read option 642, a transmit parameter option 644, a broadcast frequency parameter option 646, a device voltage parameter option 648, a broadcast frequency parameter option 650, an integral parameter option 652, and a device identity option 654. In response to selection of one or more of the options 634-654, the user may enter tuning parameters into the mobile device 104 for the handheld device 102.

Specifically, in response to selecting the A/D threshold option 634, the user may determine a minimum voltage level of an output from the engagement sensor for the signal to be considered a stroke. As an example, if the voltage is detected to be too low, the sensor output is likely to be a false signal. To prevent sensor output signals from being identified as false signals, this parameter may be adjusted. Similarly, in response to selection of the delay threshold option 636, a user may input a value for a minimum amount of time that the engagement sensor is triggered for the signal to be presumed to be accurate. As discussed above, if the engagement sensor outputs a signal, where the sensor was triggered for a very short time relative to a normal stroke, a determination may be made that the sensor output was an error and not an actual stroke. As such, this time may be adjusted to optimize the number of accurate strokes captured.

As an example, a determination may be made that the average stroke length is three inches for a particular user and the average speed is 6 inches per second. Accordingly, the user may adjust the minimum time threshold for counting a stroke. This adjustment may be made on by the mobile device 104 and/or may be sent to the handheld device 102 for adjustment. In the example provided above, the handheld device 102 may be configured to send all instances where the engagement sensor is triggered to the mobile device 104 and the mobile device 104 parses out the inadvertent signals. In such an embodiment, the mobile device 104 may adjust the threshold for parsing out the inadvertent signals. Similarly, some embodiments may be configured such that the handheld device 102 parses out inadvertent signals and only sends the true signals to the mobile device 104. In such embodiments, the mobile device 104 may communicate the adjustment to the handheld device 102, which may alter its logic accordingly. Other adjustments may also be made.

Returning now to FIG. 6, in response to selection of the repeat threshold option 638, the user may determine an amount of time that is the shortest allowed time between engagement sensor outputs to be considered as separate strokes. Specifically, if the engagement sensor outputs a first signal and 0.01 seconds later outputs a second signal, a determination may be made that the break in signal was accidental and the two signals should be considered part of the same stroke. Thus, the minimum time for the two signals to be counted separately may be adjusted. In response to selection of the time read option 640, a measurement of time may be provided by the user that identifies the clock cycle utilized by the processor of the handheld device 102 for sensor events, processor awake time, etc.

In response to selection of the timeout read option 642, data may be provided by the user related to an amount of time without sensor outputs required for the handheld device 102 to shutdown. In response to selection of the transmit parameter option 644, the user may determine a transmit amplitude (such as a radio frequency amplitude) for transmitting data from the handheld device 102 to the mobile device 104 and/or remote computing device 106.

In response to selection of the broadcast frequency parameter option 646, timing, frequency, and/or other data related to the transmission of data from the handheld device 102 may be determined. In response to selection of the device voltage parameter option 648, a user may determine the operating voltage of the handheld device 102, as it relates to operational limits and/or battery performance. In response to selection of the broadcast frequency parameter option 650, the user may determine the frequency at which an output signal from the handheld device 102 operates. In response to selection of the integral parameter option 652, the user may determine an algorithm that is used by logic in the handheld device 102 for making a logical decision. As an example, software updates and/or other logic may be received. In response to selection of the device identity option 654, the user may determine an identifier for the handheld device 102 as it relates to transmission of data. Additionally, in response to selection of the auto adjust option 632, one or more of the options 634-654 may be automatically selected by the handheld device 102 or other device to optimize operation of the handheld device, based on past user preferences, past user usage, and/or other determinations.

Figure 7:
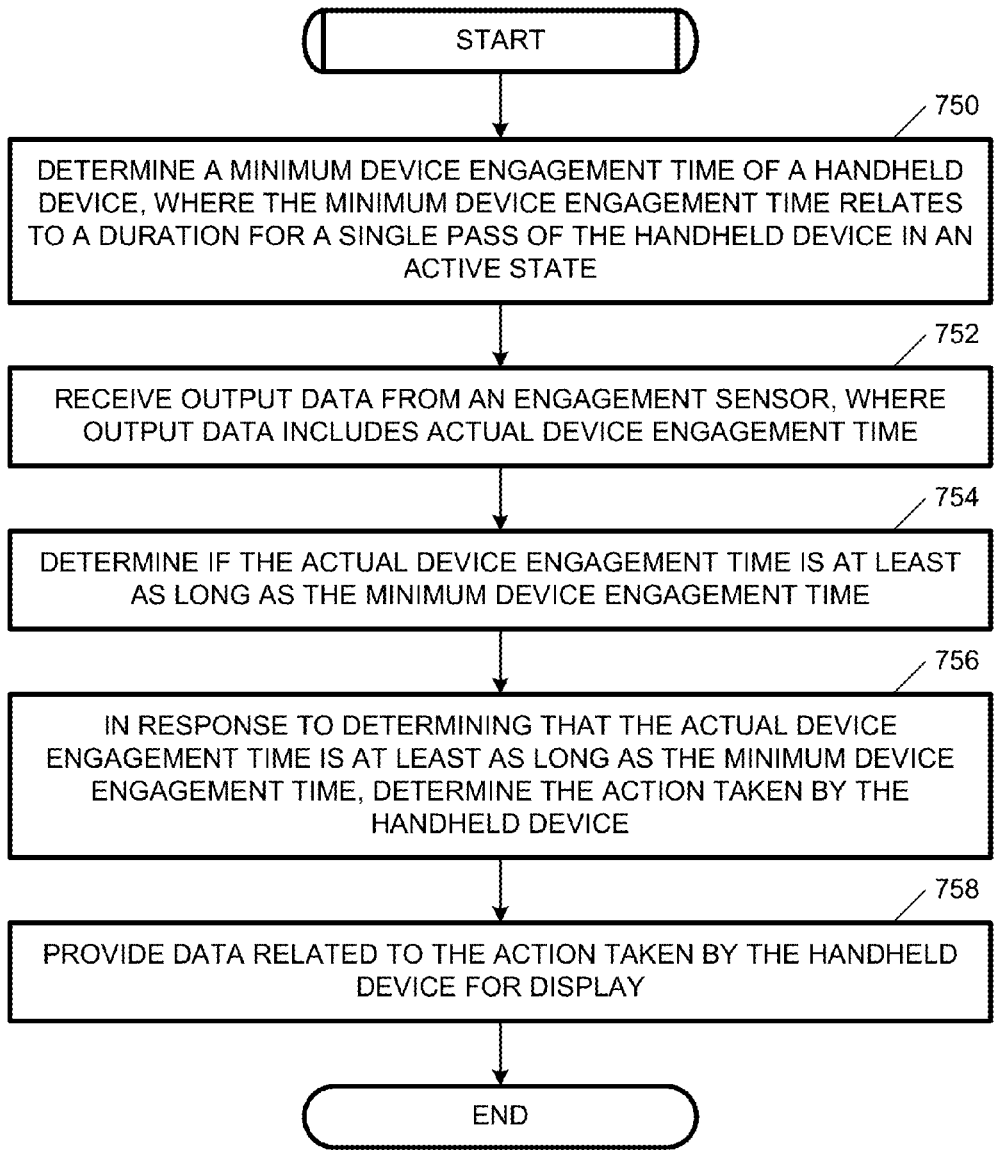
FIG. 7 depicts a flowchart for device monitoring, according to embodiments described herein.

FIG. 7 depicts a flowchart for device monitoring, according to embodiments described herein. As illustrated in block 750, a minimum device engagement time of a handheld device 102 may be determined. The minimum device engagement time may relate to a duration for a single pass of the handheld device 102 in an active state. Specifically, the handheld device 102 may be activated by an actuation of the handheld device 102, by linking the handheld device 102 with the mobile device 104, etc. Additionally, a setting may be selected (by a user or automatically) to determine a minimum device engagement time, which represents the shortest amount of time the engagement sensor will be triggered to count the triggering as a stroke (or pass). As an example, some embodiments may be configured to determine a gender of the user and, in response to determining the gender of the user, adjusting the minimum engagement time (because presumably face shaving will have shorter strokes than leg shaving). In block 752, output data may be received from an engagement sensor, where the output data includes an actual device engagement time. Specifically, the transmitting system may send a signal to the hardware and/or software on the handheld device 102 representing that the engagement sensor was triggered. This information may then be sent to the mobile device 104, the remote computing device 106, and/or processed by the hardware on the handheld device 102. In block 754, a determination may be made regarding whether the actual device engagement time is as least as long as the minimum device engagement time. In block 756, in response to determining that the actual device engagement time is at least as long as the minimum device engagement time, a determination may be made regarding the action taken by the handheld device 102. As an example, the action may include a total time from activation of the handheld device 102 to deactivation of the handheld device 102, an average length of the actual device engagement time, a temperature of water that contacts the handheld device 102; a duration of time between consecutive actual device engagements, an engagement count, a speed of the handheld device 102, an acceleration of the handheld device 102, a distance traveled by the handheld device 102, an angle of the handheld device 102 relative to a user, an angle of a first portion of the handheld device 102 relative to a second portion of the handheld device 102, an angular rotation of the first part of the handheld device 102 relative to the second portion of the handheld device 102, and/or a force against a surface, such as the user's skin. If the actual device engagement time is not at least as long as the minimum engagement time, an assumption may be made that the handheld device 102 was not actually engaged. In block 758, data related to the action taken by the handheld device 102 may be provided for display.

Figure 8:
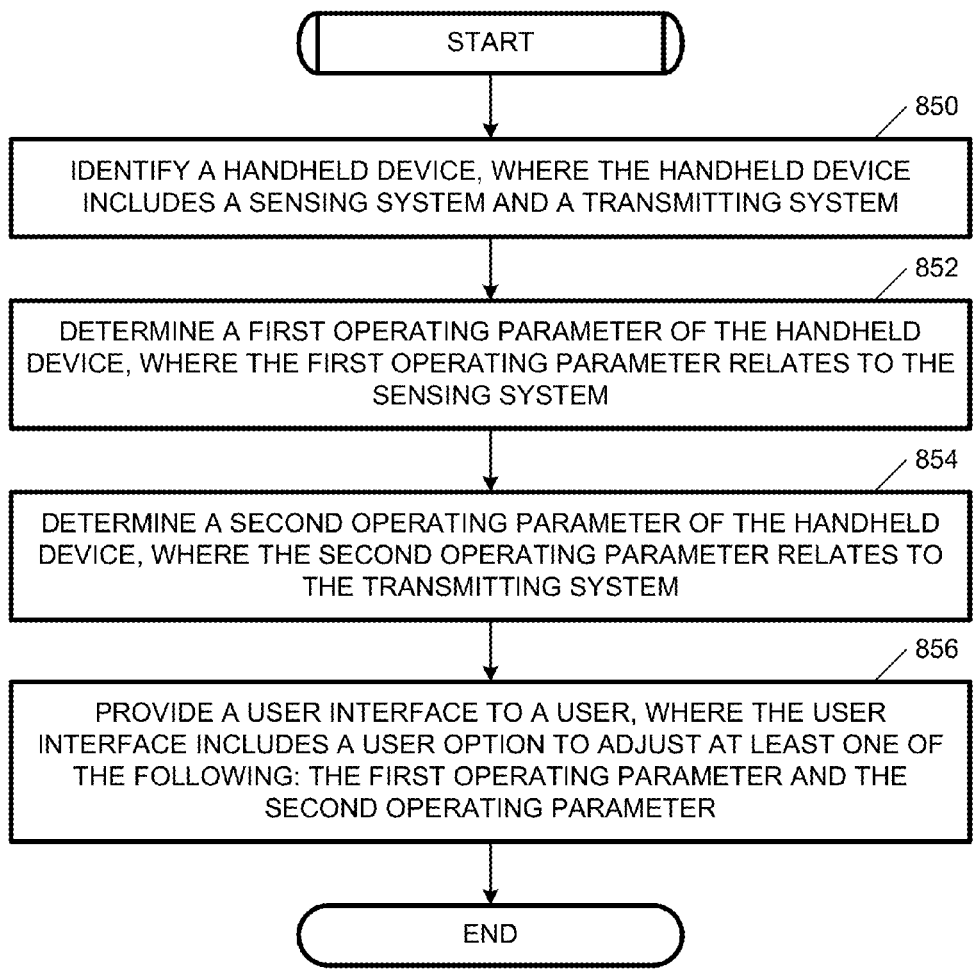
FIG. 8 depicts a flowchart for device tuning, according to embodiments described herein.

FIG. 8 depicts a flowchart for device tuning, according to embodiments described herein. As illustrated in block 850, a handheld device 102 may be identified, where the handheld device 102 includes a sensing system 212 and a transmitting system. In block 852, a first operating parameter of the handheld device 102 may be determined, where the first operating parameter relates to the sensing system 212. Specifically, the first operating parameter may include an analog to digital conversion threshold, a device engagement delay threshold, a repeat engagement delay threshold, a time read parameter, a timeout read parameter, and/or other parameter. In block 854, a second operating parameter of the handheld device 102 may be determined where the second operating parameter relates to the transmitting system. As an example, the second operating parameter may include a transmit power parameter, a broadcast frequency parameter, a device voltage parameter, an interval parameter, and/or other parameter. In block 856, a user interface may be provided for display to a user, were the user interface includes a user option to adjust the first operating parameter and/or the second operating parameter.

Additionally, some embodiments may be configured to receive environment data related to a water type, an assisting substance type, a distance from the handheld device, data related to interference with the handheld device and/or other environment data. Additionally, the handheld device 102 and/or mobile device 104 may automatically adjust the first operating parameter and/or the second operating parameter based on the environment data.

Some embodiments may also be configured to receive user input related to the first and/or second operating parameter. Based on the user input, an adjustment to the handheld device and/or mobile device may be made.

Figure 9:
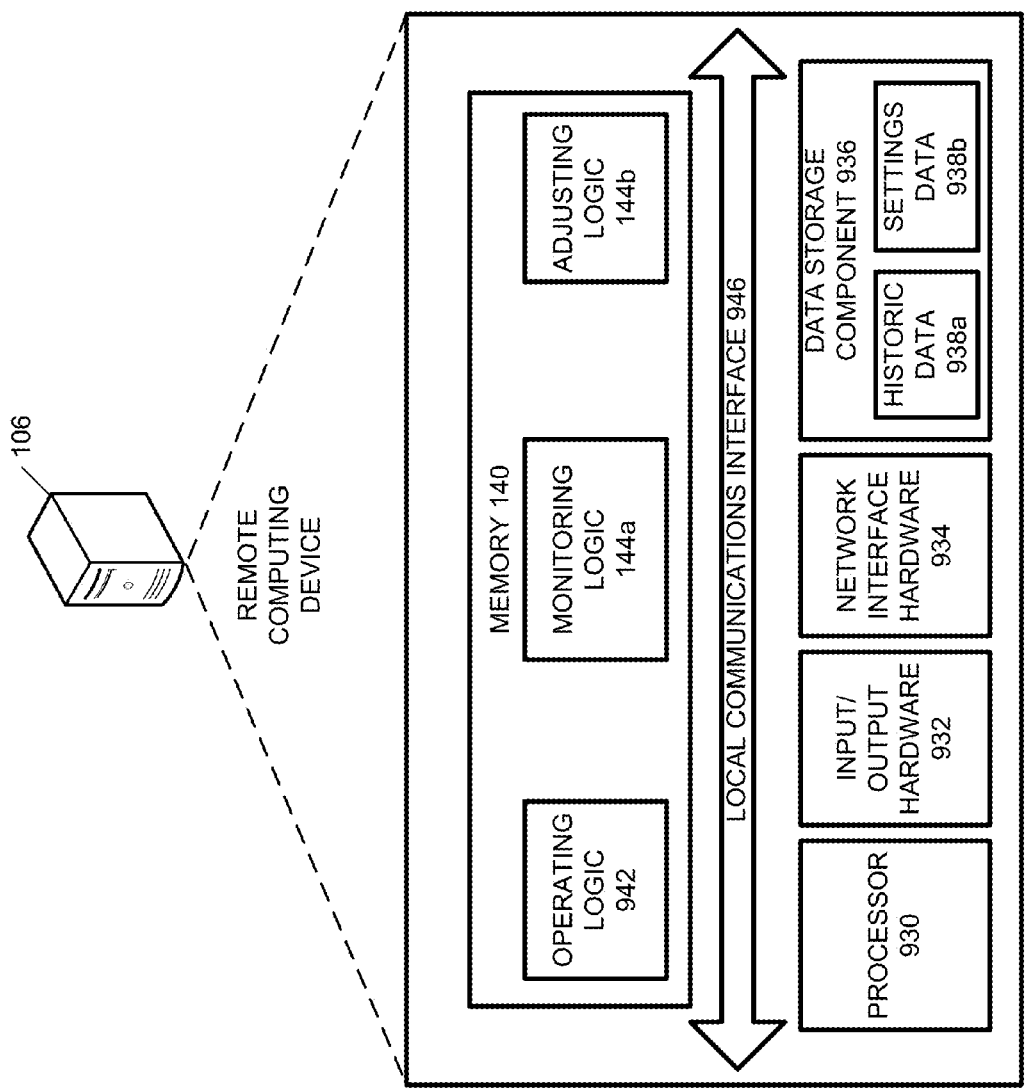
FIG. 9 depicts a computing device for device monitoring and device tuning, according to embodiments described herein.

FIG. 9 depicts a remote computing device 106 for device monitoring and device tuning, according to embodiments described herein. The remote computing device 106 includes a processor 930, input/output hardware 932, network interface hardware 934, a data storage component 936 (which stores historic data 938*a*, settings data 938*b*, and/or other data), and the memory component 140. The memory component 140 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the remote computing device 106 and/or external to the remote computing device 106.

The memory component 140 may store operating system logic 942, the monitoring logic 144*a* and the adjusting logic 144*b*. The monitoring logic 144*a* and the adjusting logic 144*b* may each include a plurality of different pieces of logic, each of which may be embodied as a computer program, firmware, and/or hardware, as an example. A local interface 946 is also included in FIG. 9 and may be implemented as a bus or other communication interface to facilitate communication among the components of the remote computing device 106.

The processor 930 may include any processing component operable to receive and execute instructions (such as from a data storage component 936 and/or the memory component 140). As described above, the input/output hardware 932 may include and/or be configured to interface with the components of FIG. 9.

The network interface hardware 934 may include and/or be configured for communicating with any wired or wireless networking hardware, including an antenna, a modem, a LAN port, wireless fidelity (Wi-Fi) card, WiMax card, mobile communications hardware, and/or other hardware for communicating with other networks and/or devices. From this connection, communication may be facilitated between the remote computing device 106 and other computing devices, such as those depicted in FIG. 1.

The operating system logic 942 may include an operating system and/or other software for managing components of the remote computing device 106. As discussed above, the monitoring logic 144*a* may reside in the memory component 140 and may be configured to cause the processor 930 to monitor usage of the handheld device 102. Similarly, the adjusting logic 144*b* may be utilized to adjust one or more settings on the handheld device 102.

It should be understood that while the components in FIG. 9 are illustrated as residing within the remote computing device 106, this is merely an example. In some embodiments, one or more of the components may reside external to the remote computing device 106. It should also be understood that, while the remote computing device 106 is illustrated as a single integrated device, this is also merely an example. In some embodiments, the monitoring logic 144*a* and the adjusting logic 144*b* may reside on different computing devices and/or the remote computing device 106 may be configured as a mobile device 104. As an example, one or more of the functionalities and/or components described herein may be provided by the handheld device 102, the mobile device 104, and/or other computing devices, which may be coupled to the remote computing device 106 via the network 100. These computing devices may also include hardware and/or software for performing the functionality described herein.

Additionally, while the remote computing device 106 is illustrated with the monitoring logic 144*a* and the adjusting logic 144*b* as separate logical components, this is also an example. In some embodiments, a single piece of logic may cause the remote computing device 106 to provide the described functionality.

Combinations:

An example is below:

A. A system for monitoring device usage, comprising:

a handheld device for performing an action, wherein the handheld device includes an engagement sensor; and a computer that includes a processor and a memory component, wherein the memory component stores logic that, when executed by the processor causes the computer to perform at least the following:

determine a minimum device engagement time of the handheld device, wherein the minimum device engagement time relates to a duration for a single pass of the handheld device in an active state;

receive output data from the engagement sensor, wherein the output data includes an actual device engagement time;

determine if the actual device engagement time is at least as long as the minimum device engagement time;

in response to determining that the actual device engagement time is at least as long as the minimum device engagement time, determine the action taken by the handheld device; and provide data related to the action taken by the handheld device for display.

B. The system of Paragraph A, wherein the computer is integral to the handheld device, wherein the handheld device further includes a transmitter, and wherein the computer utilizes the transmitter to communicate data related to a total number of engagements with a remote computing device.

C. The system of Paragraph A, wherein the computer includes a remote computing device that communicates with a local computing device that is integral with the handheld device.

D. The system of Paragraph A, wherein the action includes an actual number of passes with the handheld device and wherein the memory component further stores logic that causes the computer to perform at least the following:

provide an option for a user to identify a predicted total number of passes from activation of the handheld device to deactivation of the handheld device;

compare the predicted total number of passes with a total number of passes; and provide a result of the comparison for display.

E. The system of Paragraph A, wherein the handheld device communicatively connects to the computer in response to at least one of the following: receiving a signal from the engagement sensor indicating that the handheld device is activated, receiving actuation of a user option on the handheld device, and in response to determining deactivation of the handheld device.

F. The system of Paragraph A, wherein the handheld device comprises at least one of the following: a razor and a toothbrush.

G. The system of Paragraph A, wherein the action taken by the handheld device includes at least one of the following: a total time from activation of the handheld device to deactivation of the handheld device, an average length of the actual device engagement time, a temperature of water that contacts the handheld device; a duration of time between consecutive actual device engagements, an engagement count, a speed of the handheld device, an acceleration of the handheld device, a distance traveled by the handheld device, an angle of the handheld device relative to a user, an angle of a first portion of the handheld device relative to a second portion of the handheld device, an angular rotation of the first portion of the handheld device relative to the second portion of the handheld device, and a force against a surface.

H. A method for monitoring device usage, comprising:
determining a minimum razor engagement time of a razor device, wherein the minimum razor engagement time relates to a minimum duration required for counting a single stroke of the razor device across an length of skin;
receiving stroke data related to an actual stroke of the razor device across the length of skin, wherein the stroke data includes an actual duration of the actual stroke of the razor device across the length of skin;
determining if the actual duration is at least as long as the minimum duration;
in response to determining that the actual duration is at least as long as the minimum duration, determine an action taken by the razor device from the stroke data; and
provide data related to the action taken by the razor device for display.

I. The method of Paragraph H, further comprising providing at least a portion of the data to a server.

J. The method of Paragraph H, further comprising:
receiving tuning instructions from a remote computing device; and
altering at least one setting of the razor device, based on the tuning instructions.

K. The method of Paragraph H, further comprising communicatively connecting to a computer in response to at least one of the following: receiving a signal from the razor device, indicating that the razor device is activated, receiving actuation of a user option on the razor device, and in response to determining deactivation of the razor device.

L. The method of Paragraph H, further comprising determining at least one of the following: a total time from activation of the razor device to deactivation of the razor device, an average length of the actual duration, a temperature of water that contacts the razor device; a duration of time between consecutive actual device engagements, an engagement count, a speed of the razor device, an acceleration of the razor device, a distance traveled by the razor device, an angle of the razor device relative to a user, an angle of a first portion of the razor device relative to a second portion of the razor device, an angular rotation of the first portion of the razor device relative to the second portion of the razor device, and a force against a surface.

M. The method of Paragraph H, further comprising receiving data from an assisting device to determine data related to the action, wherein the assisting device includes at least one of the following: a shave prep container, a tooth paste container, a replacement razor, a replacement toothbrush head, a razor device container, a toothbrush container.

N. The method of Paragraph H, further comprising determining at least one of the following and, in response to determining at least one of the following, adjusting the minimum razor engagement time accordingly: a gender of a user, a past user preference, and an identity of the user.

O. A non-transitory computer-readable medium for monitoring device usage that stores logic that, when executed by a computing device, performs at least the following:
determine a minimum device engagement time of a handheld device, wherein the minimum device engagement time relates to a duration for a single pass of the handheld device in an active state, wherein the handheld device includes an engagement sensor for determining when the handheld device is engaged;
receive output data from the engagement sensor, wherein the output data relates to actual device engagement time;
determine if the actual device engagement time is at least as long as the minimum device engagement time;
in response to determining that the actual device engagement time is at least as long as the minimum device engagement time, determine an action taken by the handheld device;
provide data related to the action for display.

P. The non-transitory computer-readable medium of Paragraph O, wherein determining the action includes determining that the handheld device engages with a user wherein the logic further causes the computing device to perform at least the following:
provide an option for the user to identify a predicted total number of engagements from activation of the handheld device to deactivation of the handheld device;
compare the predicted total number of engagements with a total number of engagements; and
provide a result of the comparison for display.

Q. The non-transitory computer-readable medium of Paragraph O, wherein the logic further causes the computing device to communicatively connect to a local computing device that is integral to the handheld device in response to at least one of the following: the local computing device receiving a signal from the engagement sensor indicating that the handheld device is activated, the handheld device receiving an actuation of a user option on the handheld device, and in response to a determination of deactivation of the handheld device.

R. The non-transitory computer-readable medium of Paragraph O, wherein the handheld device comprises at least one of the following: a razor and a toothbrush.

S. The non-transitory computer-readable medium of Paragraph O, wherein the logic further causes the computing device to determine at least one of the following: a total time from activation of the handheld device to deactivation of the handheld device, an average length of the actual device engagement time, a temperature of water that contacts the handheld device; a duration of time between consecutive actual device engagements, an engagement count, a speed of the handheld device, an acceleration of the handheld device, a distance traveled by the handheld device, an angle of the handheld device relative to a user, an angle of a first portion of the handheld device relative to a second portion of the handheld device, an angular rotation of the first portion of the handheld device relative to the second portion of the handheld device, and a force against a surface.

T. The non-transitory computer-readable medium of Paragraph O, wherein the logic further causes the computing device to determine at least one of the following and, in response to determining at least one of the following, adjusting the minimum device engagement time accordingly: a gender of a user, a past user preference, and an identity of the user.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system for monitoring device usage, comprising:
   a handheld device for performing an action, wherein the handheld device comprises
      a handle portion;
      a sensing system;
      a transmitting system; and
      a cartridge connection component;
         wherein the sensing system comprises an engagement sensor to detect any of a position, an angle, and a movement of the handheld device; and
         wherein the transmitting system comprises a transmitter; and
   a computer that comprises a processor and a memory component, wherein the memory component stores logic that, when executed by the processor causes the computer to perform at least the following:
      determine a minimum device engagement time of the handheld device, wherein the minimum device engagement time relates to a shortest duration of time the engagement sensor can be triggered to count for a pass of the handheld device in an active state;
      receive output data from the engagement sensor based on a triggering of the engagement sensor during the action;
      determine an actual device engagement time based on the output data;
      determine if the actual device engagement time is at least as long as the minimum device engagement time;
      in response to determining that the actual device engagement time is at least as long as the minimum device engagement time, determine the action taken by the handheld device; and
      provide data related to the action taken by the handheld device for display.

2. The system of claim 1, wherein the computer is integral to the handheld device, wherein the computer utilizes the transmitter to communicate data related to a total number of engagements to a remote computing device based on the triggering of the engagement sensor during the action.

3. The system of claim 1, wherein the handheld device comprises a local computing device, and wherein the computer is a remote computing device that communicates with the local computing device.

4. The system of claim 1, wherein the action includes an actual number of passes with the handheld device and wherein the memory component further stores logic that causes the computer to perform at least the following:
   provide an option for a user to identify a predicted total number of passes from activation of the handheld device to deactivation of the handheld device;
   compare the predicted total number of passes with a total number of passes; and
   provide a result of the comparison for display.

5. The system of claim 1, wherein the handheld device communicatively connects to the computer in response to at least one of the following: receiving a signal from the engagement sensor indicating that the handheld device is activated, receiving actuation of a user option on the handheld device, and in response to determining deactivation of the handheld device.

6. The system of claim 1, wherein the handheld device comprises at least one of the following: a razor and a toothbrush.

7. The system of claim 1, wherein the action taken by the handheld device comprises at least one of the following:
   a total time from activation of the handheld device to deactivation of the handheld device;
   an average length of the actual device engagement time;
   a temperature of water that contacts the handheld device;
   a duration of time between consecutive actual device engagements;
   an engagement count;
   a speed of the handheld device;
   an acceleration of the handheld device;
   a distance traveled by the handheld device;
   an angle of the handheld device relative to a user;
   an angle of a first portion of the handheld device relative to a second portion of the handheld device;
   an angular rotation of the first portion of the handheld device relative to the second portion of the handheld device; and
   a force against a surface.

8. A method for monitoring device usage, comprising:
   receiving stroke data related to an actual stroke of a razor device across a length of skin, wherein the stroke data includes an actual duration of the actual stroke of the razor device across the length of skin, wherein the razor device comprises a handle portion and a sensing system, and wherein the stroke data is generated by an engagement sensor of the sensing system of the razor device;
   determining that the actual duration is at least as long as a minimum duration, wherein the minimum duration relates to a minimum razor engagement time required for counting a single stroke of the razor device across the length of skin;

in response to determining that the actual duration is at least as long as the minimum duration, determine an action taken by the razor device from the stroke data; and provide data related to the action taken by the razor device for display.

9. The method of claim 8, further comprising providing at least a portion of the data to a server.

10. The method of claim 8, further comprising:
receiving tuning instructions from a remote computing device; and
altering at least one setting of the razor device, based on the tuning instructions.

11. The method of claim 8, further comprising communicatively connecting to a computer in response to at least one of the following: receiving a signal from the razor device, indicating that the razor device is activated, receiving actuation of a user option on the razor device, and in response to determining deactivation of the razor device.

12. The method of claim 8, further comprising determining at least one of the following:
a total time from activation of the razor device to deactivation of the razor device, an average length of the actual duration;
a temperature of water that contacts the razor device; a duration of time between consecutive actual device engagements;
an engagement count, a speed of the razor device, an acceleration of the razor device;
a distance traveled by the razor device, an angle of the razor device relative to a user;
an angle of a first portion of the razor device relative to a second portion of the razor device; and
an angular rotation of the first portion of the razor device relative to the second portion of the razor device, and a force against a surface.

13. The method of claim 8, further comprising receiving data from an assisting device to determine data related to the action, wherein the assisting device comprises at least one of the following:
a shave prep container;
a tooth paste container;
a replacement razor;
a replacement toothbrush head;
a razor device container; and
a toothbrush container.

14. The method of claim 8, further comprising determining at least one of the following and, in response to determining at least one of the following, adjusting the minimum razor engagement time accordingly: a gender of a user, a past user preference, and an identity of the user.

15. A non-transitory computer-readable medium for monitoring device usage that stores logic that, when executed by a computing device, performs at least the following:
determine a minimum device engagement time of a handheld device, wherein the minimum device engagement time relates to a duration for a single pass of the handheld device in an active state, wherein the handheld device comprises a handle portion, a sensing system, a transmitting system, and wherein the sensing system comprises an engagement sensor for determining when the handheld device is engaged;
receive output data from the engagement sensor of a handheld device, wherein the output data relates to actual device engagement time;
determine if the actual device engagement time is at least as long as the minimum device engagement time;
in response to determining that the actual device engagement time is at least as long as the minimum device engagement time, determine an action taken by the handheld device; and
provide data related to the action for display.

16. The non-transitory computer-readable medium of claim 15, wherein determining the action comprises determining that the handheld device engages with a user wherein the logic further causes the computing device to perform at least the following:
provide an option for the user to identify a predicted total number of engagements from activation of the handheld device to deactivation of the handheld device;
compare the predicted total number of engagements with a total number of engagements; and
provide a result of the comparison for display.

17. The non-transitory computer-readable medium of claim 15, wherein the logic further causes the computing device to communicatively connect to a local computing device that is integral to the handheld device in response to at least one of the following: the local computing device receiving a signal from the engagement sensor indicating that the handheld device is activated, the handheld device receiving an actuation of a user option on the handheld device, and in response to a determination of deactivation of the handheld device.

18. The non-transitory computer-readable medium of claim 15, wherein the handheld device comprises at least one of the following: a razor and a toothbrush.

19. The non-transitory computer-readable medium of claim 15, wherein the logic further causes the computing device to determine at least one of the following: a total time from activation of the handheld device to deactivation of the handheld device, an average length of the actual device engagement time, a temperature of water that contacts the handheld device; a duration of time between consecutive actual device engagements, an engagement count, a speed of the handheld device, an acceleration of the handheld device, a distance traveled by the handheld device, an angle of the handheld device relative to a user, an angle of a first portion of the handheld device relative to a second portion of the handheld device, an angular rotation of the first portion of the handheld device relative to the second portion of the handheld device, and a force against a surface.

20. The non-transitory computer-readable medium of claim 15, wherein the logic further causes the computing device to determine at least one of the following and, in response to determining at least one of the following, adjusting the minimum device engagement time accordingly: a gender of a user, a past user preference, and an identity of the user.

* * * * *